United States Patent [19]
Ball

[11] Patent Number: 5,847,268
[45] Date of Patent: Dec. 8, 1998

[54] VISCOSITY MEASURING APPARATUS AND METHOD

[76] Inventor: Dean M. Ball, 4282 Pillsbury Rd., Gainesville, Ga. 30507

[21] Appl. No.: 820,167

[22] Filed: Mar. 19, 1997

[51] Int. Cl.[6] .............................. G01N 11/04; A61B 5/00
[52] U.S. Cl. ..................... 73/54.09; 73/54.04; 73/54.14
[58] Field of Search ............................... 73/54.09, 54.14, 73/54.04

[56] References Cited

U.S. PATENT DOCUMENTS

| | | | |
|---|---|---|---|
| 3,071,961 | 1/1963 | Heigl et al. | 73/55 |
| 3,234,781 | 2/1966 | Bragg | 73/55 |
| 3,353,403 | 11/1967 | Deily et al. | 73/55 |
| 3,808,877 | 5/1974 | Blair | 73/55 |
| 3,990,295 | 11/1976 | Renovanz et al. | 73/55 |
| 4,028,929 | 6/1977 | Bohm | 73/55 |
| 4,165,632 | 8/1979 | Weber et al. | 73/55 |
| 4,449,394 | 5/1984 | Hegedus | 73/55 |
| 4,539,837 | 9/1985 | Barnaby | 73/55 |
| 4,750,351 | 6/1988 | Ball | 73/55 |
| 4,793,174 | 12/1988 | Yau | 73/55 |
| 4,876,882 | 10/1989 | Yau | 73/55 |
| 5,040,410 | 8/1991 | Chu et all. | 73/54 |
| 5,172,585 | 12/1992 | Gleissle | 73/54.04 |
| 5,222,497 | 6/1993 | Ono | 128/637 |
| 5,257,529 | 11/1993 | Taniguchi et al. | 73/54.09 |
| 5,331,843 | 7/1994 | Gramatte et al. | 73/54.09 |
| 5,347,852 | 9/1994 | Mode | 73/54.04 |
| 5,616,855 | 4/1997 | Ball | 73/54.43 |

*Primary Examiner*—Hezron E. Williams
*Assistant Examiner*—J. David Wiggins
*Attorney, Agent, or Firm*—Kennedy, Davis & Kennedy, P.C.

[57] ABSTRACT

A forced flow viscosity measuring apparatus includes within a housing (13), a thermostatic air chamber (11), a measurement capillary (38) and a needle (60) in fluid communication with the capillary each contained in the chamber, and a variable speed drive mechanism (14) which dries such needle into the liquid at a speed that maintains the pressure differential constant across the length of same measurement capillary to which is attached a pressure measuring device (30) and the needle (60), and a control circuit (50). The control circuit (50) computes viscosity as a function of sensed needle (60) velocity, sensed constant pressure differential and the parameters of the capillary.

4 Claims, 3 Drawing Sheets

VISCOSITY MEASURING APPARATUS AND METHOD

TECHNICAL FIELD

This invention relates to apparatuses and methods for measuring the viscosities of liquids.

BACKGROUND OF THE INVENTION

Viscosity measurement of liquids is an essential procedure in the characterization of many liquid products including lubricants and polymers. For instance, the suitability of a lubricating oil for a particular purpose is closely related to the viscosity of the oil and to variations of the viscosity with temperature. In capillary viscosity measurement, which is a conventionally used technique, the pressure drop of a liquid flowing through a capillary is used to measure its viscosity. Typically the capillary has a very small internal diameter, such as 3 mm or less. When a liquid exhibits a high resistance to flow through the capillary, its viscosity is high, and vice versa. In using the capillary measurement technique, the equation for absolute viscosity at a given temperature, which is known as the Poiseuille equation, is:

$$\eta \frac{\pi \cdot \Delta P \cdot r^2}{8 \cdot L \cdot F}$$

where $\eta$ is the viscosity of the liquid in poise or grams per second-centimeter, and:

$\Delta P$ is the pressure drop across the capillary in dynes-second per square centimeter F is the flow rate through the capillary in cubic centimeters per second L is the length of the capillary in centimeters, and r is the internal radius of the capillary in centimeters Most polymers, including nylon, polyester, rubber, polyethylene, cellulose, polyvinylchloride and polystyrene, are routinely characterized during production by dissolving them in a solvent and then measuring the viscosity of the resulting solution. The conventional means of measuring viscosity employs a bulb-type viscometer in which the time for a fixed volume of liquid to flow through a precision bore glass capillary at a given temperature and under the influence of gravity is measured and then compared with the time for a liquid of known viscosity to flow through the capillary under the same conditions. Such viscometers are usually either of the glass single bulb type capillary or of the double bulb type. With these types of viscometers the measuring bulbs are filled with a liquid having a viscosity to be measured. The liquid is then allowed to drain under the force of gravity through the capillary and into a reservoir. The length of time, referred to as the drop time, for the liquid meniscus to pass a set of two marks on the capillary is recorded and compared with the time that a reference liquid of known viscosity takes for such passage. From this difference in times the viscosity of the test liquid can be determined.

While glass capillary viscometers are commonly used, there are a number of problems associated with their use. For instance, before a glass capillary viscometer analysis can begin, often a ten to twenty minute period must pass while the sample equilibrates to the analysis temperature. This period of time is required as a result of the low thermal conductivity of the glass capillary viscometer and of the very high dependence of the viscosity of liquids on temperature. This dependence ranges from three to nine percent per degree Celsius difference. Thus, in order to measure viscosity to one part in one thousand accuracy, the temperature must be controlled to within 0.01 degree Celsius.

The actual process of measuring viscosity with a capillary viscometer is also quite time consuming. Each measurement of the drop time requires from three to fifteen minutes, depending on the viscosity of the liquid, and must be duplicated to within 0.35 percent in order to obtain a value that can be relied upon. If the second drop time is not close enough to the first, a third or even fourth drop time must be obtained. The complete viscosity determination, from sample equilibration to measurement, and then through to viscometer cleaning, typically requires from twenty to forty minutes.

Another disadvantage of the glass bulb-type capillary viscometer is that when opaque samples are analyzed, the meniscus cannot be visually observed. This prevents the operator from observing the movement of the liquid past the two calibration marks. Special apparatus must therefore be used to analyze this type of sample. For instance, a reverse flow capillary viscometer must be constructed which measures the viscosity of liquids when the viscometer is being filled rather than while it is being drained. In this type of capillary the bulbs are positioned at the lower end of the capillary tube.

Another common problem with bulb-type capillary viscometers is that measurement errors occur when the test sample drops too rapidly within the capillary. When the liquid falls down the capillary too rapidly, a significant amount of fluid clings to the walls and the volume of liquid being measured decreases. This phenomenon decreases the volume of liquid being measured, with a proportional decrease in measurement accuracy. This occurs when the diameter of the capillary is so large that the drop time is low.

Furthermore, the viscosity value obtained from a glass capillary viscometer must be adjusted to take into account fluid density. The viscosity value obtained from a glass capillary is known as the kinematic viscosity (that is the coefficient of viscosity of a fluid divided by the density). The kinematic viscosity is directly affected by the density of the liquid. If absolute viscosity is to be measured, the density of the sample must be measured independently and the kinematic viscosity be multiplied by the density.

Finally, after analysis is completed with a glass capillary viscometer, the viscometer must be cleaned and dried before use with another analysis. This cleaning process often consumes large quantities of hazardous solvents, such as toluene, which must be disposed of as hazardous material. Furthermore, being glass and therefore fragile, breakage of capillary viscometers is common.

In some instances, electronic equipment and pumps have been added to standard capillary viscometers in order to increase the accuracy and speed of measurement. For instance, reciprocating pumps and vacuums have been used in conjunction with capillaries to create a flow of fluid through a capillary at a constant pressure. Additionally, light sources and photodetectors have been employed for precisely determining the drop time. Some modified capillaries require multi-passage systems with pumping mechanisms to maintain pressure across a capillary constant. However, these devices do not provide an accurate measure of the flow rate of, the sample and still suffer from the problems previously mentioned.

Non-capillary viscometers and rheometers have also been developed to measure the viscosity of multiple liquid samples as well as melt flows. Such viscometers include rotation viscometers. A typical rotation viscometer comprises two concentric cylinders, the inner or outer cylinder being rotated in or rotated around the fixed outer or inner cylinder. With such a viscometer, the test liquid is placed between two cylinders and either of the cylinders is rotated around its axis. However, rotation viscometers have several disadvantages. Several measurements must be made on the same liquid sample at different shear stresses. Calculations of viscosity from these devices are troublesome and lead to noticeable errors as they require graphical differentiation of logarithmic values. Special and unstable flows take place at high rotating rates. Furthermore, the devices which are difficult to clean, must be cleaned after each measurement. Finally, rotational viscometers do not easily render themselves to automation.

Still other non-capillary viscometers have been developed which measure viscosity using different scientific principles. For instance, differential viscometers, such as those made by the Viscotek company, are based on a fluid analog of the wheatstone bridge, and allow solvents to flow continuously through a bridge network. The differential pressure across the bridge is zero until the sample solution in a reservoir is injected into one of the capillaries. The differential pressure begins to rise until it reaches a steady state value proportional to the specific viscosity of the solution. The viscosity is then calculated from an extensive series of equations. Such a device is limited in its viscosity range and measures viscosity by comparison.

Finally, other non-capillary type viscometers have been developed which calculate viscosity by first determining the flow rate of a liquid passing from a vessel at a given pressure to a vessel at a lower pressure and by the change rate of the internal vessel pressure. Such devices calculate the viscosity of the liquid from shear stress and shear rate by using a lengthy array of calculations. While each of these viscometers have proven superior to the bulb-type capillary viscometer, they still require extensive time to operate and are often not fully automated. Many of these types of devices are limited in their viscosity measurement range.

Accordingly, it is seen that a need remains for a viscosity measuring apparatus which reduces or overcomes many of the problems associated with those of prior art. It is to the provision of such that this invention is primarily directed.

SUMMARY OF THE INVENTION

In a preferred form of the invention the viscosity of a liquid contained in a container is measured by forcing the liquid through a capillary of a given size by driving a needle into the container at a speed that maintains the pressure differential constant across the length of the capillary, and calculating the viscosity of the liquid as a function of the needle speed, pressure differential and capillary size.

In another form of the invention an apparatus for measuring viscosity of a liquid contained in a container has a capillary of a given radius and length, and a needle in fluid communication with the capillary. A means is provided for driving the needle into the container of liquid at variable speeds which forces liquid into and through the capillary. A means is provided for measuring the pressure difference across the length of the capillary and for adjusting the speed of the needle to a test speed that maintains the measured pressure difference across the capillary constant. The apparatus also includes a means for determining this test speed and calculating the viscosity of the liquid from the measured constant pressure differential, the needle test speed and the size of the capillary.

DETAILED DESCRIPTION

Figure 1:
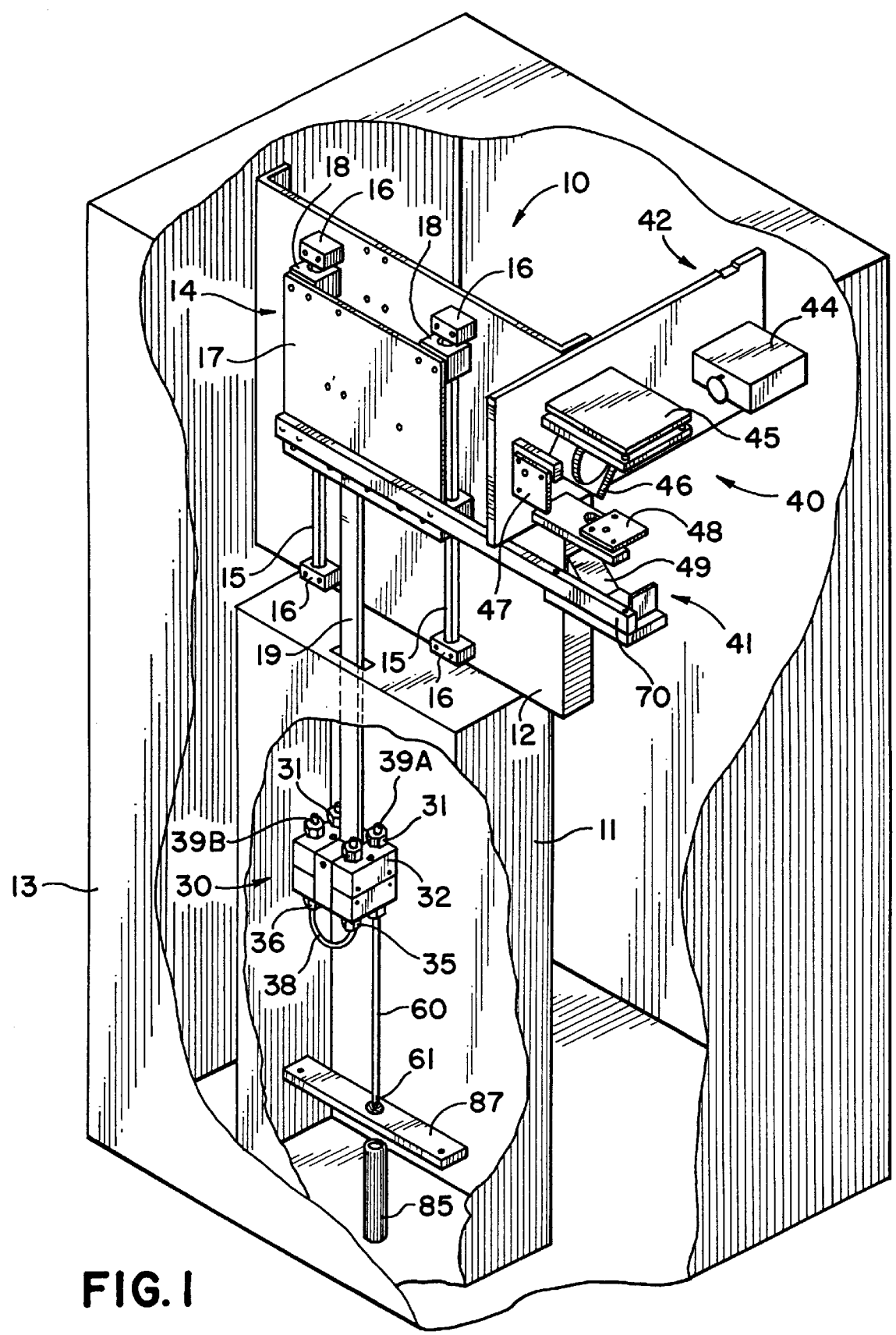
FIG. 1 is a cutaway perspective view of a forced flow viscosity measuring apparatus that embodies principles of the invention in a preferred form.
Figure 2:
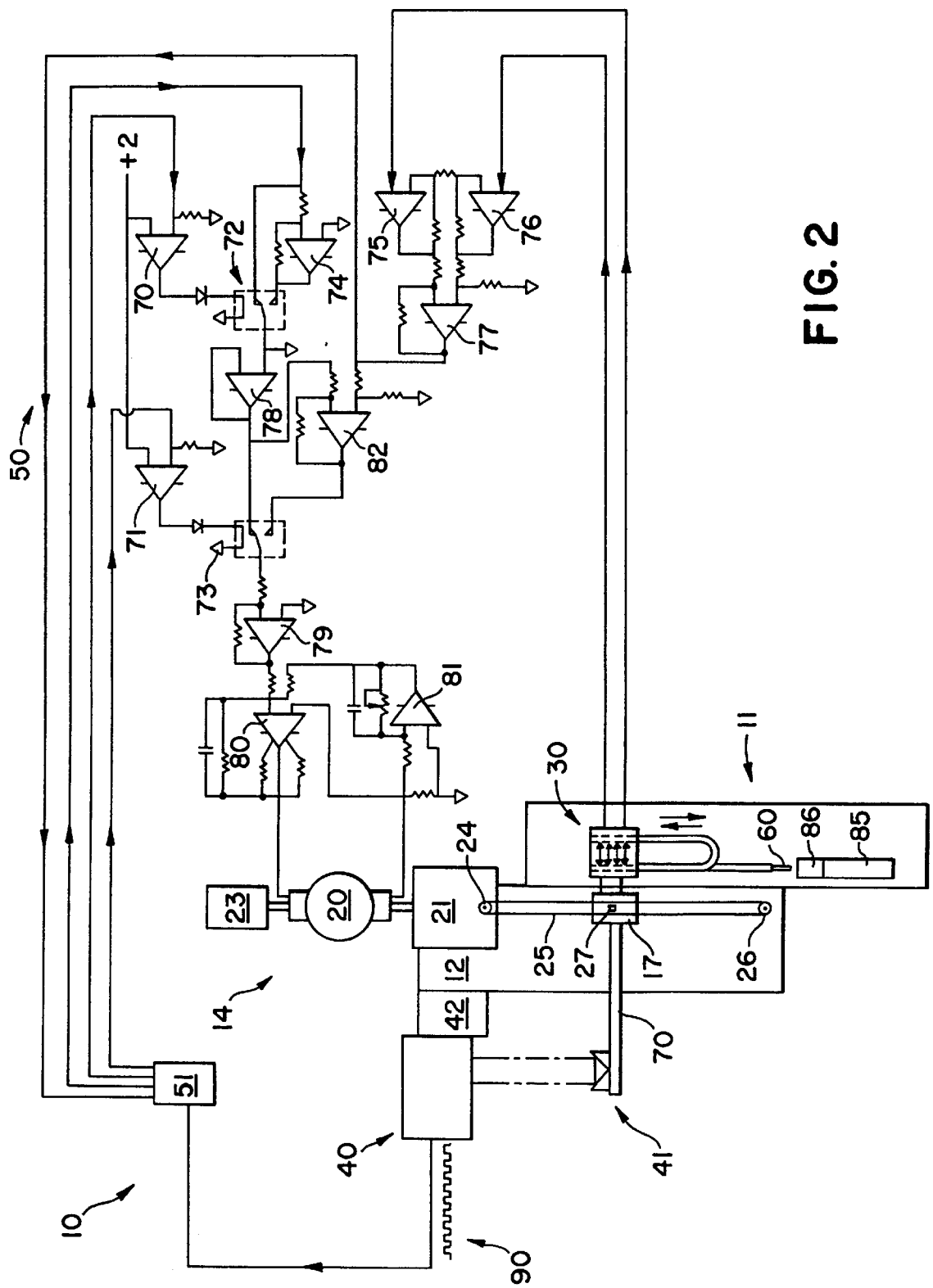
FIG. 2 is a block diagram illustrating the relationship between the various elements of the forced flow viscosity measuring apparatus of FIG. 1 in a forced flow viscosity measuring system, including a schematic of the control circuit.

With reference next to the drawings, there is shown a forced flow viscometer 10 that comprises a thermally controlled chamber 11 in a housing 13 shown in FIGS. 1 and 2. Exemplary of the details of such a chamber is the one shown and described in U.S. Pat. No. 5,616,855. Such a chamber has access doors through which containers of liquids to be tested may be introduced and placed beneath liquid extraction devices. Typically means are provided for controlling the temperature within the chamber to within 0.01° C.

A mounting plate 12 is mounted inside the housing 13. A drive mechanism 14 is coupled to the mounting plate 12. A pressure measuring device 30 is mounted to the drive mechanism 14. A laser interferometer 40 has a section 41 coupled to the drive mechanism 14 and another section which is mounted to a second mounting plate 42. The viscosity measuring apparatus 10 also has a control circuit 50 with a microprocessor 51 to which the differential pressure measuring device 30, a drive mechanism 14, and the interferometer 40 are electrically connected.

As seen in FIG. 1, the drive mechanism 14 has a pair of parallel vertical rods 15 mounted at each end to the mounting plate 12 by brackets 16, and a moveable plate 17 coupled to the parallel rods 15 for reciprocal movement there along by bearing blocks 18 journaled upon the rods. A vertical arm 19 descends from the moveable plate 17. As seen in FIG. 2, the drive mechanism 14 also includes a conventional D.C. motor 20 mechanically coupled to a gear box 21 and position sensing potentiometer 23. The gear box 21 is mounted to mounting plate 12 on the side opposite the moveable plate 17. The gear box 21 has a conventional drive pulley 24 upon which is mounted an endless loop drive cable 25 which is also coupled to a stationary pulley 26 fixedly mounted to mounting plate 12. The moveable plate 17 has a coupler 27 fixedly mounted to the drive cable 25.

Figure 3:
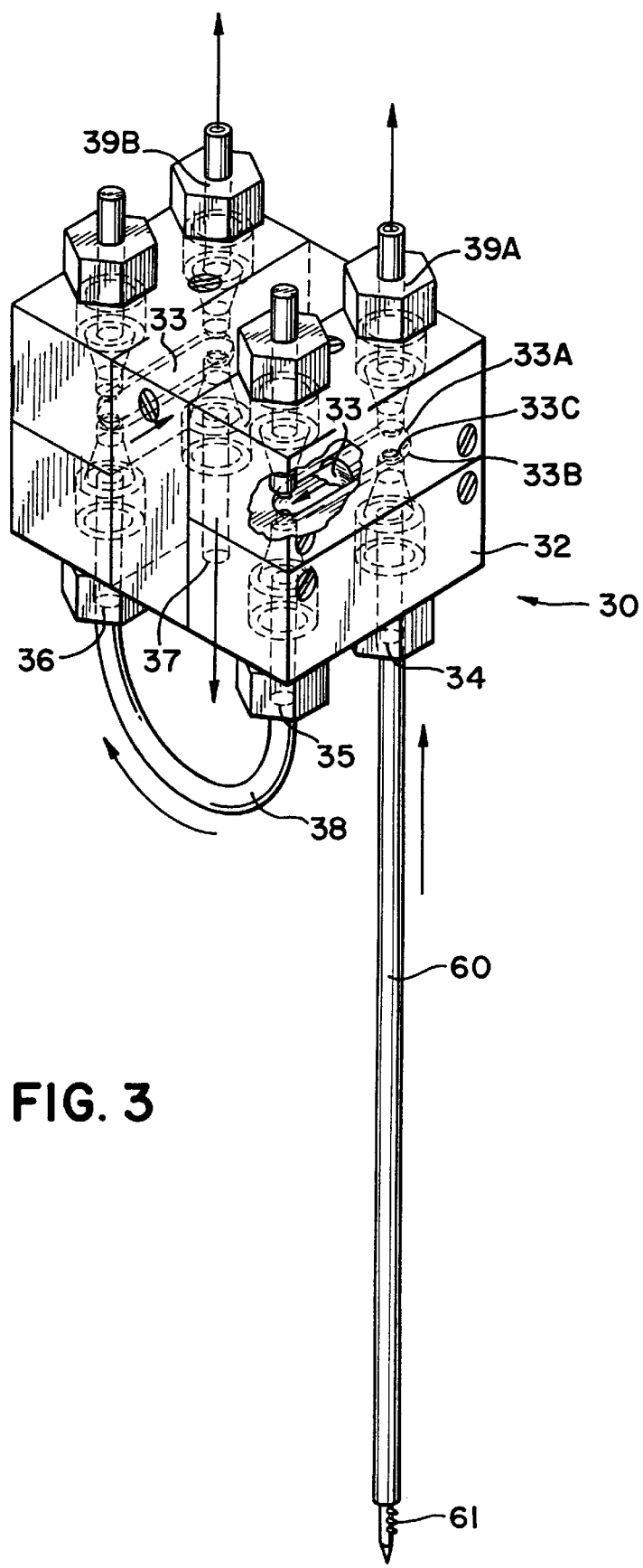
FIG. 3 is an enlarged view of the pressure measuring device shown in FIG. 1.

As seen in FIG. 3, the pressure measuring device 30 has a conventional differential pressure transducer 31 coupled to the lower end of the vertical arm 19. The differential pressure transducer 31 include a manifold 32 having a channel 33 therethrough, an inlet 34, a capillary inlet 35, a capillary outlet 36 and an outlet 37 in fluid communication with a waste reservoir (not shown). The channel 33 is divided along its length into an upper half 33A and a lower half 33B and has a gold foil seal 33C separating the two halves. Gold foil of 0.01 mm thickness, as seen in FIG. 3, separates silicon fluid in the upper half of the channel of the differential pressure transducer, from the sample fluid from the inlet and outlet of the measurement capillary. Gold foil is used because it is non-permeable and is comprised of a noble element which is unreactive with the samples being tested. Furthermore, the gold foil is malleable as not to interfere with pressure readings of the differential pressure transducers. A measurement capillary loop 38 extends from the capillary inlet 35 to the capillary outlet 36 in an orientation depending from the manifold 32.

The measurement capillary loop 38 preferably has a uniform diameter across its length, with the capillary being made of stainless steel and being silver-soldered to insure the continuous flow of liquid. The inside radius of the measurement capillaries used varies according to the viscosity of the sample to be tested, with the more high viscosity samples requiring capillaries of larger diameter. Examples of the dimensions of the measurement capillaries used in the apparatus are listed in the following Table A:

TABLE A

Dimensions of tubing having an internal volume of 0.100 milliliters that will produce a pressure drop of 1 PSI at a flow rate of 0.5 milliliter per second for various liquid viscosities

| | | |
|---|---|---|
| Viscosity (Cp): 0.1 | Bore Radius (Cm): 0.015 | Length (Cm): 148.8 |
| Viscosity (Cp): 1.0 | Bore Radius (Cm): 0.021 | Length (Cm): 69.0 |
| Viscosity (Cp): 10.0 | Bore Radius (Cm): 0.032 | Length (Cm): 32.0 |
| Viscosity (Cp): 100.0 | Bore Radius (Cm): 0.046 | Length (Cm): 14.9 |
| Viscosity (Cp): 1000.0 | Bore Radius (Cm): 0.068 | Length (Cm): 6.9 |

Dimensions of tubing having an internal volume of 0.100 milliliters that will produce a pressure drop of 1 PSI at a flow rate of 1.0 milliliter per second for various liquid viscosities

| | | |
|---|---|---|
| Viscosity (Cp): 0.1 | Bore Radius (Cm): 0.016 | Length (Cm): 118.1 |
| Viscosity (Cp): 1.0 | Bore Radius (Cm): 0.024 | Length (Cm): 54.8 |
| Viscosity (Cp): 10.0 | Bore Radius (Cm): 0.035 | Length (Cm): 25.4 |
| Viscosity (Cp): 100.0 | Bore Radius (Cm): 0.052 | Length (Cm): 11.8 |
| Viscosity (Cp): 1000.0 | Bore Radius (Cm): 0.076 | Length (Cm): 5.5 |

The differential pressure transducer 31 also has an inlet pressure transducer 39A coupled to the inlet 34, an elongated analysis needle 60 coupled to the inlet 34, and an outlet pressure transducer 39B coupled to the outlet 37. The metal analysis needle 60 extends downward from the differential pressure transducer 31 and is in fluid communication with the measurement capillary inlet opening 35. The outlet opening 36 of the measurement capillary 38 feeds into a waste receptacle (not shown) for disposal of the tested sample. The analysis needle 60 is preferably stainless steel and of uniform diameter. The analysis needle 60 has at least one hole 61 on its side rather than at its tip end to prevent blocking of the hole during use.

The pressure transducers 39A and 39B are electrically coupled to the control circuit 50 through the microprocessor 51. It should be understood that only the intake portion of each pressure transducer extends into the thermostatic chamber 11, that is the pressure measuring device 30 and all equipment beneath it as seen in FIG. 3, as the pressure transducers are somewhat sensitive to temperature variations.

The laser interferometer 40 has a mounting plate 42 mounted to the side wall of the mounting plate 12. A laser diode 44, a silicon photo diode pulse counting monitor 45, a beam splitter 46, a first mirror 47, and a second mirror 48 are all mounted to the interferometer mounting plate 42. A retroreflector mirror 49 is mounted to an elongated arm 70, which in turn is mounted to the moveable plate 17. The laser diode 44 emits a laser beam aimed at the beam splitter 46 which bifurcates the laser beam into first and second light beams. The first light beam is emitted from the beam splitter 46 to the first mirror 47 where it is then partially reflected back to the laser diode and to the beam splitter, and reflected to the silicon photodiode 45. The second light beam is diverted to the retroreflector mirror 49 which reflects the second light path onto the second mirror 48 which in turn reflects the light back to the retroreflector 49 mirror, to the silicon photodiode 45. The mounting plate 12, with the gear box 21 attached, and the mounting plate 42, with the interferometer attached, are all solidly mounted to each other and the chamber 11 within housing 13.

With reference now to FIG. 2 and specifically regarding the electronic control circuit 50, the control circuit contains two amplifiers 70 and 71 as comparators used to turn relays 72 and 73 on and off and a signal inverter 74 is used to reverse the drive mechanism 14, as hereinafter described. Three amplifiers 75, 76, and 77 amplify the signals from the differential pressure transducer 31. An amplifier 82 serves as a difference amplifier. Two amplifiers 79 and 80 are used to drive the drive mechanism 14 when an amplifier 81 is used to sense the motor current. A microprocessor 51, preferably an IBM 486 DX is included in the control circuit to control movement of the vertical arm 19 and to calculate viscosity values. The microprocessor receives inputs from the pressure transducers 39A and 39B of the pressure measuring device 30, and from the interferometer 40, and transmits output to the drive mechanism 14 to control the drive mechanism direction and speed.

The apparatus is used in conjunction with a precision bore cylinder 85 for containing the liquid sample. The cylinder 85 is positioned to receive the analysis needle 60. The precision bore cylinder 85 has an open end and a closed end (not shown). The diameter of the cylinder 85 should be uniform to within 1 mil to allow for even volumetric delivery of the test sample. A polyethylene stopper 86 is sized and shaped to be received within the cylinder open end. The stopper 86 is constructed to allow the passage of the analysis needle 60 therethrough. An indexing tray (not shown) having several cylinder receptacles may be used to hold several cylinders at one time. Preferably, a needle stripper 87 is positioned to prevent the needle 60 from carrying the bore cylinder 85 during the needle withdrawal.

OPERATION

In operation a typical viscosity analysis proceeds in the following manner. An operator pours the liquid sample to be analyzed in the precision-bore cylinder 85, to a level of approximately three quarters full, and the stopper 86 is then forced into the cylinder open end. The operator then places the sample cylinder in the thermostatic air chamber 11, within the housing 13, in a position beneath the analysis needle 60, or within the indexing tray if provided. The chamber door is then closed and the control circuit 50 is initiated. The control circuit energizes the drive motor 20 so as to cause the moveable plate 17 and thus the pressure measuring device 30 to move downward. This causes the analysis needle 60 to be driven downward at a constant rate, for instance two centimeters per minute and through the stopper 86. The motor 20 drives the vertical arm 19 down at a constant speed by applying a 1 to 2 volt signal to the motor speed/pressure input and with switches 72 and 73 in the off position. As the motor 20 drives the vertical arm 19 downward and the needle 60 begins to penetrate the stopper 86, the amplifier 81 will sense the added, power needed and maintains the motor speed at a constant velocity. After the needle 60 penetrates the stopper 86, the liquid is then forced through the needle 60 and into the manifold 32 through the inlet 34 opening. The liquid then travels through the channel 33B and into the measurement capillary 38. The liquid then exits the manifold 32 through the measurement capillary outlet 36 and outlet 37 and passes into the waste receptacle.

As the liquid begins to flow up the needle 60 and through the measurement capillary 38, the pressure transducers 39A and 39B measure the liquid pressure at the inlet 34 and outlet 37 respectively, and generate corresponding signals which are relayed through the control circuit 50 for monitoring. As the pressure drop across the capillary passes a preset threshold level (for example from 0.25 to 0.5 psi), the microprocessor 51 sends a signal to the amplifier 71 to switch the feedback from constant motor speed mode to constant pressure mode (the switch 73 is turned on). The differential pressure transducer 31 transmits a signal to a feedback switch on the motor 20 to change the velocity of the drive mechanism from a constant linear motion to one which maintains a constant pressure drop across the length of the measurement capillary. This may be, for example, one pound per square inch or 40 centimeters of water pressure. At the same time, the computer sets the motor speed/pressure input signal to a constant level (for example 3 volts) so that the motor is driven faster or slower in order to maintain a constant pressure during the remainder of the analysis as a response to changes in pressure readings of the differential pressure transducer 31.

The interferometer 40 measures the linear distance traveled by the vertical arm 19 by employing the interference caused by having two monochromatic light beams on identical pathways and measuring the distance travelled over a defined period of time. Use of an interferometer enables the system to measure distance to within one half wavelength of the laser light, or about 0.5 microns. This method of measuring distance is used to calculate changes in distance travelled over a period of time in order to derive needle speed and liquid flow rate.

As the constant pressure is maintained across the measurement capillary 38, the light beams in the interferometer 40 passing across the silicon photo diode 45 are recorded as a series of pulses 90 as the retroreflector mirror 49 moves downward. A constant flow and a constant pressure is thus established across the capillary. This pulse rate provides a very accurate measurement of the distance of the needle 60 into the precision-bore cylinder 85.

The exact flow rate is then calculated by the microprocessor 51 from the equation:

$$F = \frac{\pi r^2 \Delta d}{\Delta t}$$

F is the flow rate in cubic centimeters per second
r is the radius of the cylinder in centimeters
$\Delta d$ is the increment of linear motion in centimeters
$\Delta t$ is the increment of time in seconds The flow rate, pressure drop, capillary radius and capillary length are then entered into the Poiseuille Equation by the microprocessor 51 to provide a direct measurement of the absolute viscosity of the liquid.

The feedback switch is again switched to constant motor speed by turning the switch 73 off. The remaining switch 72 is turned on to reverse the drive mechanism 14 and withdraw the analysis needle 60 from the sample being analyzed. The process is repeated until all of the samples are analyzed.

The flow measurement in the forced flow viscosity measuring apparatus is made continuously after the sample is flowing in the capillary. No use of cleaning solvent is necessary in the forced flow viscometer. Any residual sample remaining along the measurement capillary is forced into the waste receptacle with the onset of the second sample. In this fashion, the samples themselves act as cleaning agents for the viscometer. Any overlap of residual sample has minimal effect on the analysis of viscosity, in light of the volume of new test sample passing through the measurement capillary. In this regard, the internal volume of the measurement capillary 38 is approximately 0.1 ml while the volume of test sample in the cylinder 85 is as much as 5 ml.

Alternatively, the flow rate may be held constant and the pressure calculated. In addition, the precision bore cylinder samples 85 can be moved with respect to the needle 60. This alternative is more difficult to accomplish however, as it usually results in the unnecessary spillage of the test sample. Although any means may be used for precisely measuring the linear motion of the vertical arm 19 as the liquid is forced through the measurement capillary 38, the interferometer 40 has been selected for its capability of accurately measuring linear motion. Also, no calibration is necessary because of the precisely known wavelength of light used. Furthermore, it should be understood that in the alternative a drive shaft may be used as an alternative to the pulley system. However, the pulley system, is preferred as it prevents the drive mechanism from breakage should a solid object impede the path of the mechanism.

It should be noted that in the just-described forced flow viscometer apparatus, the liquid-air meniscus is not measured as in conventional glass viscometry. Therefore, the problems associated with measuring opaque samples and with samples of liguid volume, layer or residul clinging to the sides of glass walls is eliminated. Since this viscosity measurement is in absolute viscosity, the need to convert the kinematic viscosity value through a density factor to absolute viscosity is eliminated. Finally, the cleaning of the apparatus is simpler and the risk of viscometer breakage is reduced with the forced flow viscosity measuring apparatus than with conventional glass capillary viscometers.

This apparatus is an improvement over the conventional glass capillary measurement apparatus as the measurement is made with a thin walled metal capillary. Metal is preferable over glass as it has a thermal conductivity several hundred times higher than glass, although glass is the preferred material for the precision-bore cylinder. The metal capillary can be fabricated with much thinner walls as well. Both of these factors reduce the amount of time required for the liquid sample to thermally equilibrate. This, in turn reduces the total analysis time required.

It thus is seen that a forced flow viscosity measuring apparatus and method for measuring viscosity is now provided which allows a user to rapidly and accurately test for the viscosity of a liquid without the risks normally associated with a glass capillary viscometer.

Though the forced flow viscosity measuring apparatus and method have been shown and described in preferred form, many modifications, additions, and deletions may be made thereto without departing from the spirit and scope of the invention as set forth in the following, claims.

I claim:

1. Apparatus for measuring the viscosity of a liquid contained in a container which comprises:

a capillary of a given radius and length:

a needle in fluid communication with said capillary:

means for driving said needle into the container at variable speeds thereby forcing liquid into and through said capillary;

means for measuring the pressure differential across the length of said capillary:

means for adjusting the speed of said needle to a test speed that maintains the pressure differential across said capillary;

means for determining the test speed comprising an interferometer; and means for calculating the viscosity of the liquid from the measured constant pressure differential, the needle test speed and capillary radius and length.

2. Apparatus for measuring the viscosity of a liquid container in a container that is plugged with a plug comprises:

a capillary of a given radius and length;

a hollow needle in fluid communication with said capillary having a tip and an entry adjacent said tip and a shoulder;

needle driving means for driving said needle tip through the plug to locate said needle entry inside the plugged container and to bring said needle shoulder against the plug and for then driving said needle and plug together into the container at variable speeds thereby forcing liquid into and through said capillary;

means for measuring the pressure differential across the length of said capillary, and means for calculating the viscosity of the liquid as a function of the measured pressure differential, the needle and plug speeds and the capillary radius and length.

3. A method of measuring the viscosity of a liquid which comprises the steps of placing the liquid in a container having a cylindrical bore and an open end, plugging the container open end with a needle penetratable stopper, driving a needle that is in fluid communication with a capillary through the stopper sufficiently to establish fluid communication via the needle between the liquid in the container and a capillary of given length and radius disposed outside the container, driving both the needle and the stopper into the container thereby forcing liquid from the container into and through the capillary, and calculating the viscosity of the liquid as a function of the pressure differential, needle speed and capillary radius and length.

4. The method of claim 3 wherein the speed of the driven needle is adjusted to maintain the pressure differential constant across the capillary.

* * * * *